United States Patent [19]

Wang et al.

[11] Patent Number: 4,880,519
[45] Date of Patent: Nov. 14, 1989

[54] GAS SENSOR ELEMENT

[75] Inventors: Da Y. Wang, Lexington; Daniel T. Kennedy, Burlington, both of Mass.; Burton W. MacAllister, Jr., Hudson, N.H.

[73] Assignee: GTE Laboratories Incorporated, Waltham, Mass.

[21] Appl. No.: 198,029

[22] Filed: May 24, 1988

[51] Int. Cl.$^4$ ............................................. G01N 27/46
[52] U.S. Cl. .................................... 204/425; 204/424; 204/426; 204/427
[58] Field of Search ........................... 204/15, 421–429

[56] References Cited
U.S. PATENT DOCUMENTS

| | | | |
|---|---|---|---|
| 3,546,086 | 12/1970 | Sayles | 204/427 |
| 3,691,023 | 9/1972 | Ruka et al. | 204/15 |
| 3,844,920 | 10/1974 | Burgett et al. | 204/428 |
| 3,907,657 | 9/1975 | Heijne | 204/15 |
| 4,121,989 | 10/1978 | Shum et al. | 204/428 |
| 4,152,232 | 5/1979 | Otsuka et al. | 204/428 |
| 4,300,990 | 11/1981 | Maurer | 204/426 |
| 4,304,652 | 12/1981 | Chiba | 204/426 |
| 4,310,401 | 1/1982 | Stahl | 204/426 |
| 4,384,935 | 5/1983 | DeJong | 204/425 |
| 4,391,691 | 7/1983 | Linder et al. | 204/425 |
| 4,450,065 | 5/1984 | Yamada et al. | 204/426 |
| 4,466,880 | 8/1984 | Torii et al. | 204/428 |
| 4,472,247 | 9/1984 | Rohr et al. | 204/425 |
| 4,498,968 | 2/1985 | Yamada et al. | 204/425 |
| 4,505,806 | 3/1985 | Yamada | 204/425 |
| 4,505,807 | 3/1985 | Yamada | 204/425 |
| 4,540,479 | 9/1985 | Sakurai et al. | 204/427 |
| 4,547,281 | 10/1985 | Wang et al. | 204/424 |
| 4,568,443 | 2/1986 | Asayama et al. | 204/426 |
| 4,571,285 | 2/1986 | Nakazawa et al. | 204/425 |
| 4,574,627 | 3/1986 | Sakurai et al. | 204/426 |
| 4,578,172 | 3/1986 | Yamada et al. | 204/426 |
| 4,601,793 | 7/1986 | Asayama et al. | 204/425 |
| 4,634,514 | 1/1987 | Nishizawa et al. | 204/425 |
| 4,639,305 | 1/1987 | Shibata et al. | 204/424 |
| 4,647,364 | 3/1987 | Mase et al. | 204/425 |
| 4,650,560 | 3/1987 | Ueno | 204/425 |
| 4,655,901 | 4/1987 | Mase et al. | 204/426 |
| 4,659,435 | 4/1987 | Brothers et al. | 204/426 |
| 4,668,375 | 5/1987 | Kato et al. | 204/426 |
| 4,691,165 | 9/1987 | Ishiguro et al. | 338/34 |
| 4,701,739 | 10/1987 | Sasaki | 338/34 |
| 4,717,464 | 1/1988 | Oshima et al. | 204/427 |
| 4,718,999 | 1/1988 | Suzuki et al. | 204/425 |
| 4,732,663 | 3/1988 | Kato et al. | 204/426 |
| 4,759,827 | 7/1988 | Okada et al. | 204/427 |

OTHER PUBLICATIONS

Kamo et al., "Lean Mixture Sensor", 850380SAE International Congress and Exposition, Detroit, Feb. 25, 1985, pp. 69–78.
Hanland, "Internal-Reference Solid-Electrolyte Oxygen Sensor", Anal. Chem., vol. 49, No. 12, pp. 1813–1817, Oct. 1987.
Hetrick et al., "Oxygen Sensing by Electrical Pumping", Appl. Phys. Lett., vol. 38, No. 5, pp. 390–392, Mar. 1, 1981.
Hackh's Chemical Dictionary, 4th Ed., (1969), p. 611.

Primary Examiner—T. Tung
Attorney, Agent, or Firm—David M. Keay; Frances P. Craig

[57] ABSTRACT

Apparatus for measuring the concentration of oxygen in exhaust gases. A gas sensor element of yttria-stabilized zirconia ($Y_2O_3$-$ZrO_2$) has at one end a gas pump of two chambers separated by intervening $Y_2O_3$-$ZrO_2$ with an orifice extending between each chamber and the exterior of the gas sensor element. Two platinum electrodes of a first set face one chamber and two platinum electrodes of a second set face the other chamber. The gas sensor element is mounted in an insulating mounting collar in close contact with two ceramic heaters of resistance heating elements on silicon nitride substrates. The mounting collar is clamped between a shield member encircling the gas pump of the sensor element and a housing member by threaded clamping nuts. The shield member has one or more apertures therein to admit exhaust gases to be analyzed to the gas pump of the sensor element. The housing member has an electrical connector at one end which is spaced from the sensor element for providing electrical connections to the sensor element and ceramic heaters.

11 Claims, 4 Drawing Sheets

GAS SENSOR ELEMENT

CROSS-REFERENCE TO RELATED APPLICATIONS

This application is related to subject matter disclosed and claimed in application Ser. No. (198,024) entitled "Gas Sensor and Heater Assembly" and in application Ser. No. (198,028) entitled "Gas Sensing Apparatus", both filed concurrently herewith and assigned to the assignee of the present application.

BACKGROUND OF THE INVENTION

This application relates to gas sensing. More particularly, it is concerned with gas sensors employing solid electrolyte material which ionically conducts in the presence of a gas.

Various techniques and apparatus have been developed for determining the concentration of individual gases, such as oxygen, in a gas mixture, such as an exhaust gas. With some of these techniques it is difficult to determine the oxygen concentration in the range from about 0.1% to 20%. With certain types of gas sensors it is difficult to maintain accuracy over a period of time. Some techniques provide output information which varies logarithmically rather than linearly with the concentration of oxygen in the gas mixture. Some sensors are insensitive to slight changes in the partial pressure of oxygen, and therefore subject to inaccuracy. Other techniques involve complex electronic circuitry for controlling the operation of the sensing apparatus and for carrying out the measurements.

In one technique a solid electrolyte material which exhibits ionic conduction in the presence of oxygen is employed in an electrochemical gas pump. The oxygen concentration in the gas mixture is determined by the diffusion-limited current flow through the solid electrolyte material. This technique provides a signal output which is linearly proportional to the oxygen concentration in the gas mixture. A simple power supply provides a constant voltage to the electrodes of the pump. A series resistor is used to generate an output signal which is proportional to the concentration of oxygen in the gas being analyzed.

Sensors of this type require energy in the form of an applied voltage. The applied voltage needed is a function of current density, temperature and oxygen concentration. If the applied voltage is low or the temperature is low or the oxygen concentration is high, the relationship observed between the pumping current and the oxygen concentration is non-linear. If the applied voltage is too high or the temperature is too high or the oxygen concentration is low, other oxygen-containing ingredients such as $H_2O$ and $CO_2$ or the solid electrolyte material itself may dissociate contributing to faulty current in the output signal. In addition the pumping of the oxygen through the solid electrolyte material consumes energy, and the electrolyte ohmic polarization of the material is also a function of temperature and the current density. Thus, at high current density or low temperature extra voltage is needed to overcome the resistance of the electrolyte material.

Because of these problems, previously available sensors based on this technique have a limited temperature range of operation. In addition the electrodes of some sensors are exposed to gas flow. After a period of use the electrodes can shift the amount of applied voltage required, and thus lead to errors in the output signal. Heating elements are required in order to maintain a proper operating temperature for the sensor. Heating elements tend to have short lifetimes due to the mechanical instability of their materials at the high operating temperature. Certain devices have pressure-dependent output signals because of the diffusion mechanism involved in the operation of the gas pump. Most of the devices presently available require fairly high voltage in order to be operable, thus creating the possibility of faulty dissocation currents at the resulting high temperature.

SUMMARY OF THE INVENTION

A gas sensor element in accordance with the present invention comprises a body of solid electrolyte material exhibiting ion conduction in the presence of a gas to be detected. A first chamber is located within the body with passage between the first chamber and the exterior of the body. A second chamber within the body is spaced from the first chamber. Passage is provided between the second chamber and the exterior of the body. A first electrode has a tab portion facing the first chamber, and a second electrode has a tab portion facing the second chamber. The gas being detected is pumped from one chamber to the other chamber through the intervening solid electrolyte material upon the application of a voltage between the first and second electrodes.

For a better understanding of the present invention, together with other and further objects, advantages, and capabilities thereof, reference is made to the following disclosure and appended claims in connection with the above-described drawings.

DETAILED DESCRIPTION

The sensor element as described herein employs a body of a solid electrolyte material which exhibits ionic conduction in the presence of a gas, specifically oxygen. The material which is well known for providing this phenomenon with oxygen is yttria ($Y_2O_3$)-stabilized zirconia ($ZrO_2$).

Figure 1:
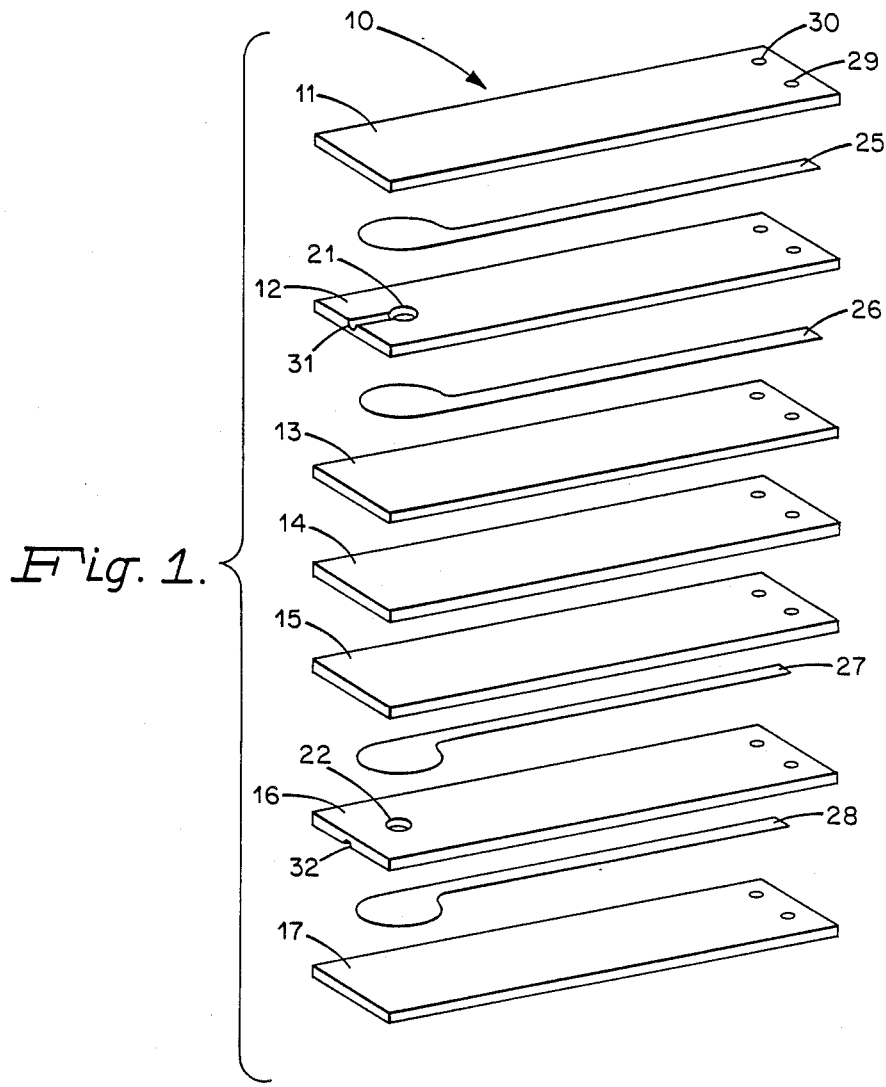
FIG. 1 is an exploded view of the components of a gas sensor element in accordance with the present invention.

The sensor element 10 is illustrated in an exploded view in FIG. 1. The sensor element 10 is composed of seven layers or laminations of yttria-stabilized zirconia 11-17. The laminations 11-17 are fabricated from yttria-stabilized zirconia powder which is a mixture of 92 mole percent of zirconia powder and 8 mole percent of yttria powder. Specifically the mixed powder is designated as TZ-8Y yttria-stabilized zirconia powder purchased from Toyo Soda USA, Inc., Atlanta, Georgia. A slurry is prepared from the yttria-stabilized zirconia powder and a binder of polyvinyl butyral, specifically Cerbind #73216 binder solution from Tam Ceramics, Inc., Niagara Falls, N.Y. The slurry is 54% by weight powder and 46% by weight binder. The mixture is ball milled for 18 hours in a milling media of zirconia balls. After mixing, the slurry is exposed to a vacuum of 30 mm Hg for 1-2 minutes to ensure that no trapped air remains in the slurry. The slurry is cast into a film with a doctor blade setting of 52 mils. The film is dried in open air for 3-4 hours, and after drying the film thickness is approximately 10-12 mils. The film is cut into suitable dimensions for the rectangular laminations, for example 1.9 inches by 0.426 inch.

Holes or openings 21 and 22 which will form gas chambers in the sensor element are produced as by punching through two laminations, the next-to-the-uppermost lamination 12 and the next-to-the-lowermost lamination 16. The openings may, for example, be 0.250 inch in diameter.

Electrodes are formed on certain of the laminations. The electrodes are of a porous conductive material which adsorbs oxygen and acts as a catalyst in dissociating oxygen into ions. The particular material used is platinum. Electrodes 25, 26, 27, and 28 are formed on the uppermost lamination 11, the lamination next below the next-to-the-uppermost lamination 13, the next-above the next-to-the-lowermost lamination 15, and the lowermost lamination 17, respectively. The electrodes are formed on the laminations by screen printing platinum ink onto the appropriate surface. Specifically the platinum ink used is designated as A4338 and is purchased from Engelhard Corp., East Newark, N.J. The ink is applied through a #325 mesh screen.

Each of the electrodes has an enlarged tab portion at one end which is the same size as the chamber openings 21 and 22. The tabs are located in the laminations so that the tabs of the electrodes of each set face each other across the appropriate chamber of the assembly. The electrodes extend along the length of the associated laminations and terminate at end portions of the laminations so as to be adjacent to openings or holes labelled 29 and 30. The holes 29 and 30 are formed in the laminations after assembly of the laminations as will be discussed hereinbelow. The electrodes are arranged on the associated laminations such that the upper electrodes 25 and 26 constituting one set are accessible only at openings 29 and electrodes 27 and 28 constituting a second set are accessible only at openings 30.

Passage between each chamber and the exterior of the sensor element for the gas being analyzed is provided by orifices 31 and 32 which are formed between the chambers 21 and 22, respectively, and the exterior during the laminating process. Alternatively, passage between each of the chambers 21 and 22 and the exterior of the sensor element may be provided by employing uppermost and lowermost laminations 11 and 17 which are porous in the regions above and below the chambers 21 and 22, respectively. In order to form the orifices 31 and 32 a plastic wire or other suitable filamentary material which is easily expended is placed between laminations 11 and 12 and between laminations 16 and 17 as the laminations are stacked for laminating. Lamination is performed at a temperature of 60° C. with the laminations pressed together under a pressure of 1000 pounds per square inch in a vacuum of 30 mm Hg for a period of from 10 to 15 minutes. Disks of ashless filter paper are placed inside the openings 21 and 22 before the laminating process to prevent the walls of the chambers from collapsing during the laminating process.

Figure 2:
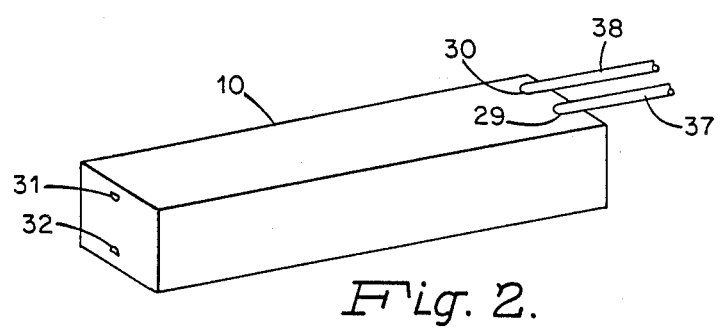
FIG. 2 is a perspective view of an assembled gas sensor element in accordance with the present invention.

After lamination the orifices 31 and 32 (FIG. 2) from the chambers 21 and 22, respectively, to the edge surface of the body are formed by burning away the filamentary material placed prior to lamination. The holes 29 and 30 are drilled through the laminated stack or body. The resulting body which is in the shape of a generally rectangular parallelepiped is then subjected to a bake out and sintering procedure. The temperature of the body is raised from room temperature to 400° C. over a period of 15 hours, and from 400° C. to 1500° C. over a period of 2 hours. The body is heated for 1 hour at 1500° C., and then cooled to room temperature over a 2 hour period. This process is carried out in open air. In the completed gas sensor element as illustrated in FIG. 2 each of the chambers 21 and 22 is approximately 0.175 inch in diameter and 0.0025 inch in height. The orifices 31 and 32 are about 0.0015 inch in diameter and about 0.05 inch in length from the chamber to the exterior edge surface of the sensor element.

As illustrated in FIG. 2 lead wire 37 which may be of 5 mil silver wire is attached to the two upper electrodes 25 and 26 through openings 29. Similarly lead wire 38 is attached to the two lower electrodes 27 and 28 through openings 30. The lead wires 37 and 38 are looped through their respective holes 29 and 30. Platinum paste is applied to ensure good electrical contact. The lead wires 37 and 38 are covered with fiberglass tubing for insulation and protection.

The gas sensor element 10 of FIGS. 1 and 2 forms an oxygen pump adjacent to the narrow edge surface at one end of the sensor element. A voltage applied between electrodes 25 and 26 of one set and electrodes 27 and 28 of the other set causes oxygen entering one of chambers 21 or 22 by way of orifice 31 or 32, respectively, to ionize. Ions flow through the yttria-stabilized zirconia to the other chamber. The current flows is a measure of the concentration of oxygen in the gas mixture to which the gas sensor element is exposed.

Figure 3:
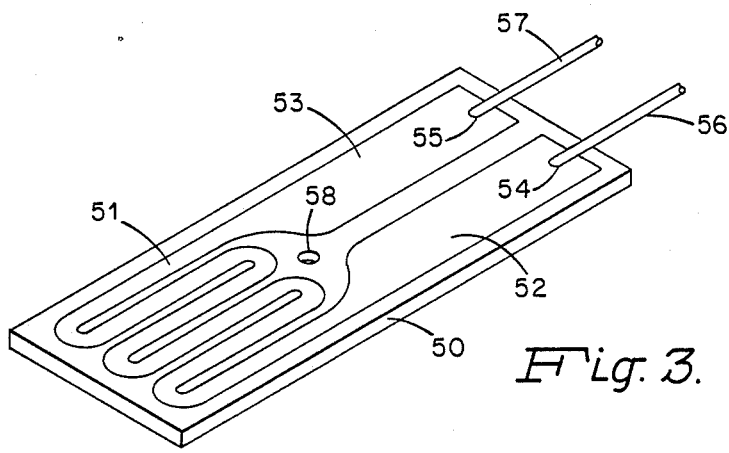
FIG. 3 is a perspective view of a ceramic heater employed in apparatus in accordance with the present invention.

The apparatus employs two ceramic heaters 50 which are assembled with the gas sensor element 10. Each ceramic heater 50 as illustrated in FIG. 3 employs a substrate of a rectangular piece of silicon nitride ceramic material. The substrate is approximately 1.2 inches by 0.3 inches and is 40 mils thick. The silicon nitride material is densified silicon nitride. Specifically, the material is formed by employing $Al_2O_3$, $Y_2O_3$, or MgO as a densification aid and may, for example, be formed as described in U.S. Pats. Nos. 4,383,958, 4,603,116 and 4,608,354.

A resistance heating element 51 in a zig-zag pattern and conductive leads 52 and 53 therefrom are formed on a flat major surface of the ceramic substrate by screen printing. For example, platinum ink #5544 from Electro-Science Labs, King of Prussia, Penna., is applied through #325 mesh screen. After the pattern of heating element 51 and leads 52 and 53 is applied, the substrates are fired in air. The temperature is raised from room temperature to 1250° C. over a period of 2 hours, firing at 1250° C. is carried on for 10 minutes, and cooling to room temperature is over a period of 2 hours. Holes 54 and 55 are formed in the printed conductors 52 and 53, respectively, at the end of the heater substrate which is spaced from the resistance heating element 51. Wire leads 56 and 57 of 5 mil silver wire pass through the holes 54 and 55 and make electrical contact to the conductors 52 and 53, respectively. A silver paste is applied to ensure good physical and electrical contact, and the wire leads 56 and 57 are protected with fiberglass sleeving. In some of the ceramic heaters an opening 58 is made through the substrate in a region not coated by the conductive material but closely adjacent to the resistance heating element 51.

Figure 5:
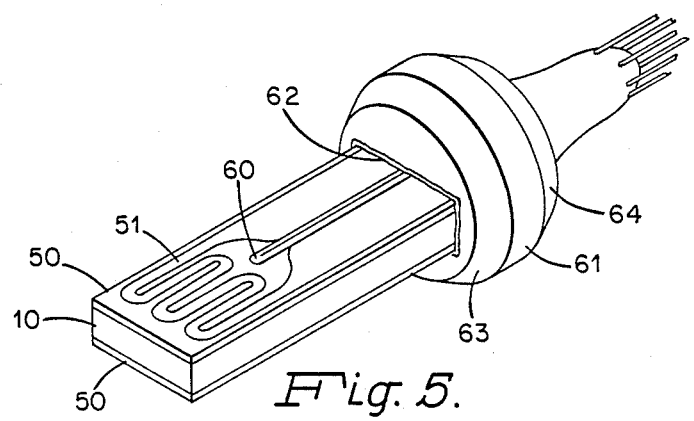
FIG. 5 is a perspective view of a portion of the apparatus of FIG. 4.
Figure 4:
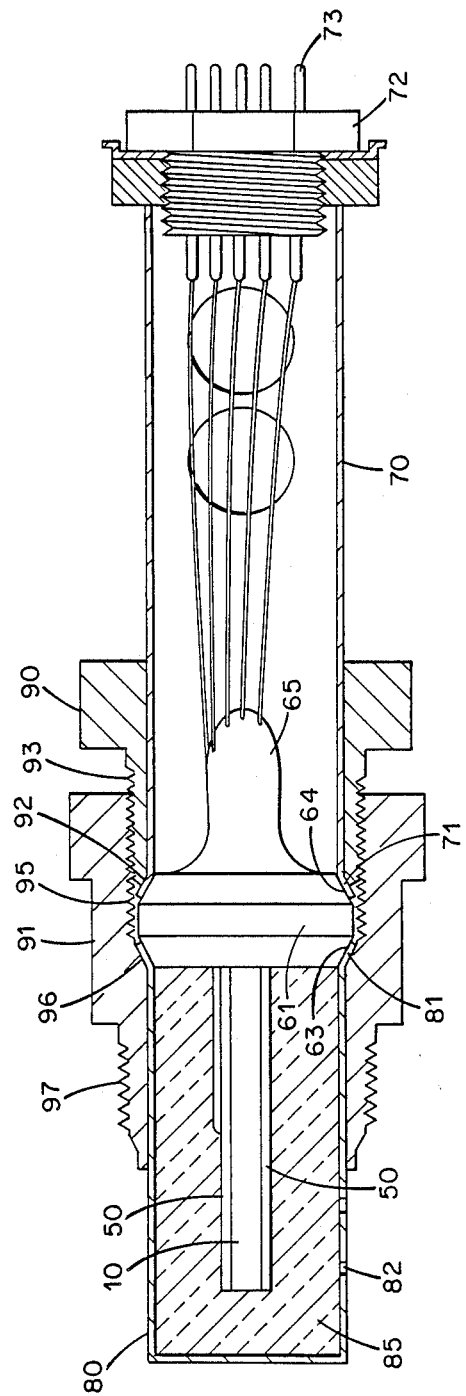
FIG. 4 is an elevational view in cross-section of gas sensing apparatus in accordance with the present invention.

FIG. 4 illustrates gas sensing apparatus employing a gas sensor element 10 sandwiched between two ceramic heaters 50 and supported in a housing which is adapted for mounting as in an engine exhaust line from an internal combustion engine. As illustrated in FIG. 5, the gas sensor element 10, the two ceramic heaters 50, and also a thermocouple 60 are mounted in a mounting collar 61. The flat major surface of each ceramic heater 50 opposite the surface containing the heating element 51 is in close physical and heat transmitting contact With a major surface of the gas sensor element 10. The mounting collar 61 is fabricated from an insulating ceramic for example #502-600 machinable ceramic purchased from Leeds and Northrop Company, Philadelphia, Penna. The mounting collar 61 is of circular cross-section and has chamfered or tapered edges 63 and 64 on the forward and rearward sides of its periphery.

The gas sensor element 10 and ceramic heaters 50 extend through a central opening 62 in the mounting collar 61. The resistance heater elements at the ends of the ceramic heaters 50 are closely adjacent to the gas pump at the end of the gas sensor element 10 and lie on the forward side of the mounting collar 61. The opposite ends of the gas sensor element and the ceramic heaters which have the lead wires attached thereto extend from the rearward side of the mounting collar 61. The thermocouple 60 fits within the opening 58 in the uppermost ceramic heater 60 and its lead wires 66 and 67 pass through the opening 62 to the rearward side of the mounting collar 61.

The assembled elements are sealed within the opening 62 of the ceramic mounting collar 61 by a suitable ceramic cement 65, for example standard 3333 foreign joint cement purchased from Leeds and Northrop Company, Philadelphia, Penna. After the cement is applied, it is air dried for 24 hours at room temperature followed by a 1 hour anneal in an oven at 100° C. The cured ceramic cement 65 is in the form of a mass completely surrounding the ends of the assembled elements on the rearward side of the mounting collar 61. The cement 65 adheres to the surface of the mounting collar forming a gas-tight seal around the elements and sealing the opening 62. The lead wires from the gas sensor element, ceramic heaters, and thermocouple pass through the cement 65 without disrupting the gas-tight seal.

A hollow cylindrical housing member 70 has an outwardly flared portion or flange 71 at one end. A standard electrical connector 72 with seven contact members 73 extending therethrough is mounted at the other end of the housing member 70. The lead wires from the assembled elements pass through the hollow cylindrical member and are connected to the contacts 73 of the connector 72 to enable electrical connections to be made thereto. The flange 71 at the end of the housing member 70 abuts the chamfered surface 64 of the mounting collar 61 and is held in close physical contact therewith as will be explained hereinbelow.

The active portions of the assembled elements containing the gas pump and resistance heaters which extend from the forward side of the mounting collar 61 are encircled by a shield member 80. The shield member which preferably may be of stainless steel is of cylindrical shape and is closed at one end. The other end has an outwardly flared portion or flange 81 for mating with the chamfered surface 63 of the mounting collar 61. The shield member 80 has one or more apertures 82 through its wall in order to enable the gas to be analyzed to enter the enclosed test chamber formed by the shield member 80 and mounting collar 61.

The test chamber is filled with porous thermal insulation 85 which encircles the portions of the assembled elements protruding beyond the forward surface of the mounting collar. The insulation 85 is preformed by wrapping fiberglass material around a dummy sensor assembly and then wrapping the fiberglass with fiberglass electrical tape. The fiberglass wrapped dummy sensor assembly is inserted into the shield member. This assemblage is fired at 650° C. for one-half hour to burn away the binders within the fiberglass insulation and tape. The dummy sensor assembly is then removed and the shield member 80 with the insulation 85 in place is assembled over the gas sensor assembly with the flange portion 81 abutting the chamfered edge 63 of the mounting collar 61.

The housing member 70 and the shield member 80 are both clamped in position against the mounting collar 61 by a clamping arrangement of a gland nut 90 and a housing nut 91. The gland nut 90 (which is placed over the housing member 70 prior to attachment of the electrical connector 72) has a chamfered or tapered surface 92 for abutting the flange 71 of the housing member 70. The gland nut has external threads 93 in the forward region adjacent to the tapered surface 92. The housing nut 91 has internal threads 95 at its rearward end for mating with the external threads 93 of the gland nut, and in its middle region has a tapered surface 96 for abutting the flange 81 of the shield member 80.

The gland nut 90 and the housing nut 91 are threaded together to urge the housing member 70 and the shield member 80 against the opposite sides of the mounting collar 61. The tapered surface 92 of the gland nut 90 clamps the flange 71 of the housing member 70 against the chamfered surface 64 of the mounting collar 61, and the tapered surface 96 of the housing nut 91 clamps the flange 81 of the shield member 80 against the chamfered surface 63 of the mounting collar 61. The physical connections between the housing nut 91, the shield member 80, and the mounting collar 61 are gas-tight seals. The housing nut 91 has a threaded external surface 97 at the forward end for mounting the apparatus with the shield member 80 protruding into a gaseous atmosphere to be analyzed.

Figure 6:
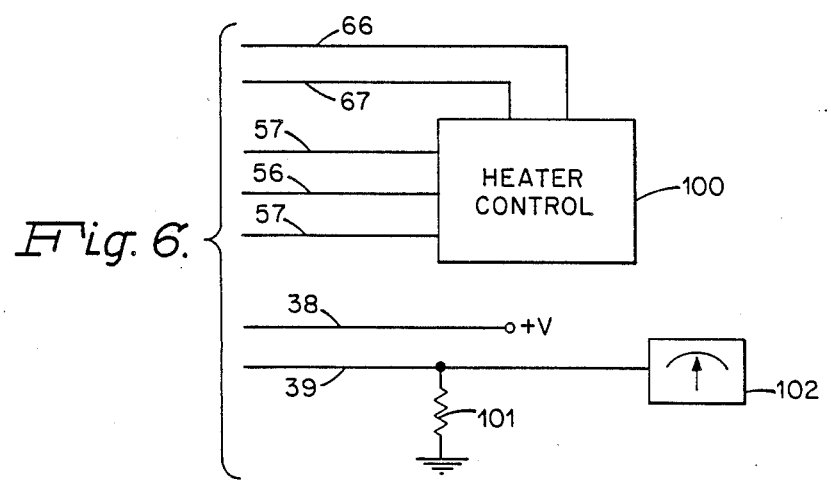
FIG. 6 is a schematic drawing of the electrical circuitry employed in conjunction with the apparatus of FIG. 4.

FIG. 6 is a schematic diagram illustrating the electrical connections to the apparatus for measuring the concentration of oxygen in a gas mixture. The leads 56 and 57 from the two ceramic heaters 50 and the leads 66 and 67 from the thermocouple 60 are connected to a heater control 100. (Leads 56 are shown connected in common.) The heater control provides electrical power to the ceramic heaters 50 at from 24 to 30 volts AC. Their temperature is monitored by the thermocouple 60, and the heater control 100 operates to maintain the gas sensor assembly at the desired temperature level for operation of the apparatus. One of the leads 38 of the gas sensor element 10 is connected to a positive source of voltage (about 3 volts DC) and the other lead 37 is connected through a series resistor 101 to ground. The potential across the resistor 101 is measured by a suitable instrument 102 to determine the current flow through the gas sensor element 10.

Figure 7:
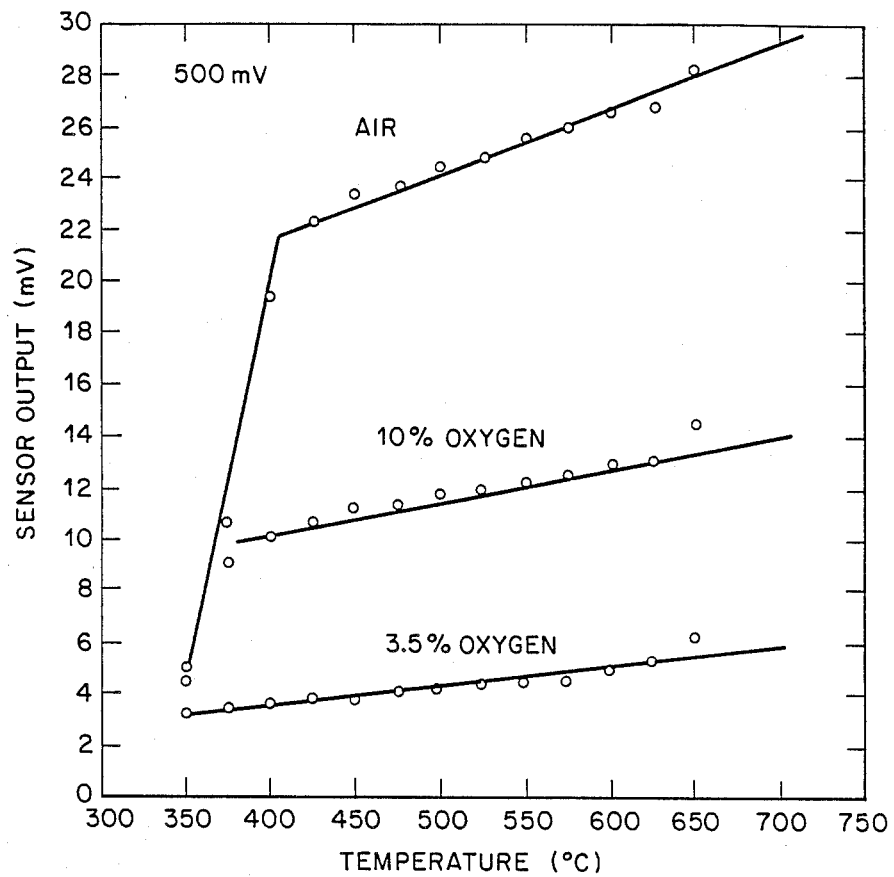
FIG. 7 is a graph illustrating curves of the output measurements of gas sensing apparatus at various concentrations of oxygen at different temperatures.

FIG. 7 is a plot of the measured output of a gas sensor element as described in detail hereinabove at different operating temperatures. The applied voltage is such as to produce 500 millivolts of applied polarization across the two sets of electrodes and a series resistor 101 of 100 ohms. The apparatus as described can measure oxygen concentration between 0.1% and air at temperatures from 450° C. to 800° C. The apparatus is relatively simple and uncomplicated and may be approximately of standard automobile spark plug size and configuration. As can be seen the measured output current is linear with respect to the concentration of oxygen in the exhaust gas being analyzed. With the device as described the limiting current density is kept low, specifically at 450° C. with air as the reference gas the current density range is between 0.8 mA/cm$^2$ and 3 mA/cm$^2$. Since the apparatus requires only 500 millivolts of applied polarization, no reduction of the solid electrolyte material will occur.

The use of the double electrode design with a set of two electrodes at each chamber provides high pumping efficiency. The electrodes are completely enclosed except at the chambers with only tiny orifices providing access of the gases to the exposed electrode surface. Thus the electrodes are well protected from gas erosion and contamination. The silicon nitride heaters provide temperature stability during operation of the gas pump. The performance and service life of the silicon nitride heaters is superior by virtue of the thermal shock resistance of the silicon nitride material.

The gas sensor assembly may include a thermocouple which is located in good position for monitoring the heat produced by the ceramic heaters and transmitted to the gas sensor element. Different modifications of the shield member may be employed. For pressure dependent measurements and rapid response to changes in oxygen concentration in the gas several apertures are provided in the portion of the shield member exposed to the exhaust gas. For pressure independent measurements and slower response to changes in oxygen concentration, a single aperture is provided in the shield member rearwardly of the forward end of the housing nut with passage provided between the housing nut and the shield member for the exhaust gas being tested.

While there has been shown and described what is considered a preferred embodiment of the present invention, it will be obvious to those skilled in the art that various changes and modifications may be made therein without departing from the invention as defined by the appended claims.

What is claimed is:

1. A gas sensor element comprising
   a body of solid electrolyte material exhibiting ion conduction in the presence of a gas to be detected;
   a first chamber within said body;
   passage between said first chamber and the exterior of the body for a gas to be analyzed;
   a second chamber within said body spaced from said first chamber with material of said body intervening between said first and second chambers;
   passage between said second chamber and the exterior of the body for said gas to be analyzed;
   a first set of two electrodes, a tab portion of each facing each other across said first chamber; and
   a second set of two electrodes, a tab portion of each facing each other across said second chamber;
   so that a voltage applied between said first set of electrodes and said second set of electrodes causes said gas to be detected entering one of said chambers by way of the associated one of said passages to ionize and ions to flow through the solid electrolyte material of the body intervening between the two chambers to the other of said chambers.

2. A gas sensor element in accordance with claim 1 wherein
   said body is of generally rectangular parallelepiped configuration having a major upper surface and a major lower surface;
   said first chamber is located below said upper surface, and said second chamber is located above said lower surface and directly below said first chamber with material of said body intervening between said first and second chambers;
   said passage between said first chamber and the exterior of the body for a gas to be analyzed comprises a first orifice extending from said first chamber parallel to said major surfaces and terminating at an edge surface normal to said major surfaces;
   said passage between said second chamber and the exterior of the body for said gas to be analyzed comprises a second orifice extending from said second chamber parallel to said major surfaces and terminating at an edge surface normal to said major surfaces;
   said two electrodes of said first set and said two electrodes of said second set are flat an planar and lie parallel to said major surfaces;
   one of the electrodes of said first set has said tab portion disposed across an upper wall surface of said first chamber, and the other of the electrodes of said first set has said tab portion disposed across a lower wall surface of said first chamber; and
   one of the electrodes of said second set has said tab portion disposed across an upper wall surface of said second chamber, and the other of the electrodes of said second set has said tab portion disposed across a lower wall surface of said second chamber.

3. A gas sensor element in accordance with claim 2 wherein
   each of said chambers is located adjacent to one of the narrower of the edge surfaces of said body;
   each of said electrodes extends from said tab portion and terminates adjacent to the other of the narrower of the edge surfaces of said body;
   the two electrodes of the first set terminate closely adjacent to each other for permitting a common electrical connection to be made thereto; and
   the two electrodes of the second set terminate closely adjacent to each other for permitting a common electrical connection to be made thereto.

4. A gas sensor element in accordance with claim 3 wherein
   said electrodes are each a porous film of a conductive material which catalyzes the ionization of the gas to be detected.

5. A gas sensor element in accordance with claim 4 wherein said conductive material of said electrodes is platinum.

6. A gas sensor element comprising
a unitary bode of laminations of a solid electrolyte material which ionically conducts oxygen;
said body being of generally rectangular parallelepiped configuration with a major upper surface and a major lower surface;
each of said laminations being of generally rectangular parallelepiped configuration with a major upper surface and a major lower surface;
the next-to-the-uppermost lamination having an opening therethrough from its major upper surface to its major lower surface;
the uppermost lamination having a first electrode of a first set of a layer of conductive material adherent to the major lower surface thereof, said electrode having a tab portion disposed across said opening in the next-to-the-uppermost lamination;
the lamination next-below the next-to-the-uppermost lamination having a second electrode of the first set of a layer of conductive material adherent to the upper major surface thereof, said electrode having a tab portion disposed across said opening in the next-to-the-uppermost lamination;
the next-to-the-lowermost lamination having an opening therethrough from its major upper surface to its major lower surface located directly below said opening in the next-to-the-uppermost lamination and separated therefrom by intervening laminations of solid electrolyte material;
the lowermost lamination having a first electrode of a second set of a layer of conductive material adherent to the major upper surface thereof, said electrode having a tab portion disposed across said opening in the next-to-the-lowermost lamination;
the lamination next-above the next-to-the-lowermost lamination having a second electrode of the second set of a layer of conductive material adherent to the lower major surface thereof, said electrode having a tab portion disposed across said opening in the next-to-the-lowermost lamination;
a first orifice extending from the opening in the next-to-the-uppermost lamination to an edge surface of the lamination for providing passage for a gas to be analyzed; and
a second orifice extending from the opening in the next-to-the-lowermost lamination to an edge surface of the lamination for providing passage for the gas to be analyzed;
so that a voltage applied between said first set of electrodes and said second set of electrodes causes oxygen entering one of said openings by way of the associated orifice to ionize and ions to flow through the solid electrolyte material of the laminations intervening between the two openings to the other of said openings.

7. A gas sensor element in accordance with claim 6 wherein
each of said openings is located adjacent to one of the narrower of the edge surfaces of the associated lamination;
each of said electrodes extends from said tab portion and terminates adjacent to the other of the narrower of the edge surfaces of the associated lamination;
the electrode adherent to the uppermost lamination and the electrode adherent to the lamination next-below the next-to-the-uppermost lamination terminate closely adjacent to each other for permitting a common electrical connection to be made thereto; and
the electrode adherent to the lowermost lamination and the electrode adherent to the lamination next-above the next-to-the-lowermost lamination terminate closely adjacent to each other for permitting a common electrical connection to be made thereto.

8. A gas sensor element in accordance with claim 7 wherein
said electrodes are each a porous film of a conductive material which catalyzes the ionization of oxygen.

9. A gas sensor element in accordance with claim 8 wherein
said solid electrolyte material is yttria-stabilized zirconia.

10. A gas sensor element in accordance with claim 9 wherein
said conductive material of said electrodes is platinum.

11. A gas sensor element in accordance with claim 10 wherein
said openings are generally cylindrical of about 0.0175 inch in diameter and 0.0025 inch in height; and
said orifices are about 0.0015 inch in diameter and about 0.05 inch in length from the opening to the exterior edge surface.

* * * * *